United States Patent [19]

Weiss

[11] Patent Number: 4,806,691

[45] Date of Patent: * Feb. 21, 1989

[54] PROCESS FOR THE PREPARATION OF TERTIARY PHOSPHINE OXIDES

[75] Inventor: Erwin Weiss, Hofheim am Taunus, Fed. Rep. of Germany

[73] Assignee: Hoechst Aktiengesellschaft, Frankfurt am Main, Fed. Rep. of Germany

[*] Notice: The portion of the term of this patent subsequent to Jun. 23, 2004 has been disclaimed.

[21] Appl. No.: 905,170

[22] Filed: Sep. 9, 1986

Related U.S. Application Data

[63] Continuation-in-part of Ser. No. 756,323, Jul. 18, 1985, Pat. No. 4,675,446.

[30] Foreign Application Priority Data

Sep. 11, 1985 [DE] Fed. Rep. of Germany ....... 3532360

[51] Int. Cl.$^4$ .............................................. C07F 9/53
[52] U.S. Cl. ..................................................... 568/14
[58] Field of Search ........................................... 568/14

[56] References Cited

U.S. PATENT DOCUMENTS

| | | | |
|---|---|---|---|
| 3,988,368 | 10/1976 | Ura et al. ........................... | 568/14 X |
| 4,670,601 | 6/1987 | Kleiner et al. ...................... | 568/14 |
| 4,675,446 | 6/1987 | Weiss ................................. | 568/14 |

OTHER PUBLICATIONS

Maier, L., *Helv. Chim. Acta* 47, 120 (1964) (p. 1).
Aguiar et al. *J. Org. Chem.* 34, 3349-52 (1969).

*Primary Examiner*—Paul F. Shaver

[57] ABSTRACT

Tertiary phosphine oxides are prepared by oxidation of tertiary phosphine sulfides using $H_2O_2$ in a solvent comprising about 2–20% by weight of optionally halogenated lower aliphatic carboxylic acids and the remainder of mono- or polyhydric aliphatic or cycloaliphatic alcohols—if appropriate in mixtures with other inert solvents which are miscible with the carboxylic acid/alcohol mixture. Preferred solvents comprise acetic acid/methanol and acetic acid/ethanol mixtures.

The reaction products are final products and intermediates products in various specialized fields such as, for example, the plant protection sector and the polymers sector.

19 Claims, No Drawings

PROCESS FOR THE PREPARATION OF TERTIARY PHOSPHINE OXIDES

CROSS REFERENCE TO RELATED APPLICATION

This application is a continuation-in-part of my copending application Ser. No. 756,323, filed July 18, 1985, now U.S. Pat. No. 4,675,446, issued June 23, 1987.

Tertiary phosphine oxides are compounds of the general formula $$R_3P=O,$$

in which R=identical or different organic radicals.

They are final and intermediate products in various specialized fields such as, for example, the plant protection sector and the polymers sector.

A series of different methods is known for their preparation. Some of these methods start from tertiary phosphine sulfides, which are converted to the corresponding phosphine oxides by means of an oxidative treatment. These methods present themselves above all when the respective tertiary phosphine sulfides are easily accessible, so that the roundabout route to the phosphine oxides via the sulfides is the more advantageous route compared to other methods for the preparation of phosphine oxides.

The oxidative conversion of the tertiary phosphine sulfides to the corresponding phosphine oxides can occur, for example, by means of $SOCl_2$, by means of $KMnO_4$ or alternatively by means of $HNO_3$; cf. the article by L. Maier "Organische Phosphorverbindungen" [Organic phosphorus compounds] in Helvetica Chimica Acta 47, p. 120-132, particularly p. 124/125 (1964). In this literature citation, the following reaction equations are specified for the oxidation using the 3 reagents mentioned:

$(ClC_6H_4)_3PS + SOCl_2 \longrightarrow (ClC_6H_4)_3PO + S_2Cl_2$ $(CH_3C_6H_4)_3PS + KMnO_4 \xrightarrow{\text{pyridine}} (HOOCC_6H_4)_3PO$ $(C_6H_5)_3PS + HNO_3 \text{ conc.} \longrightarrow (m\text{-}O_2NH_6H_4)_3PO$ The strongly corrosive action of thionyl chloride $SOCl_2$ and the formation of the strongly smelling disulfur dichloride in this reaction are disadvantageous for the method using thionyl chloride.

The oxidation using $KMnO_4$ in pyridine consistently supplies only moderate yields of phosphine oxide and proceeds—as can be seen from the reaction equation above—with oxidation of the alkyl group on the aromatic nucleus to the carboxyl group when nuclear-alkylated aromatic phosphine sulfides are employed.

In the case of the reaction using concentrated nitric acid, a nitration of the aromatic nuclei present occurs simultaneously, in addition to the formation of the phosphine oxide.

A more favorable method for the oxidation of tertiary phosphine sulfides to the corresponding phosphine oxides is the hydrogen peroxide method published by A. M. Aguiar et al. in J. Org. Chem. 34, p. 3349 to 3352, particularly p. 3351, right-hand column, final paragraph (1969). The method was described with reference to the oxidation of dimethyl-1-butynylphosphine sulfide using an approximately 75% excess of $H_2O_2$ in methanol:

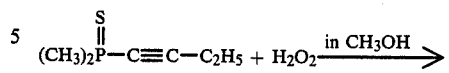

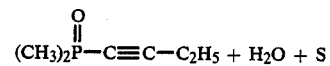

After allowing the preparation to stand for 2 days and working it up in a corresponding manner, the stated yield of dimethyl-1-butynylphosphine oxide was 61%. This method is also not satisfactory due to the long reaction time, the merely moderate yield and also the necessity of working up the hydrogen peroxide employed in excess.

The method was improved by the process, proposed in patent application P 3,426,721.2, for the preparation of tertiary phosphine oxides by means of oxidative treatment of tertiary phosphine sulfides using $H_2O_2$ in a solvent; the process comprises using a solvent which contains at least about 20% by weight, preferably at least about 50% by weight, of—optionally halogenated—lower aliphatic carboxylic acids and/or their anhydrides, and the remainder of other inert solvents which are miscible therewith. It is particularly preferable in this case to use only—optionally halogenated—aliphatic $C_1$-$C_6$-carboxylic acids and/or their anhydrides, particularly only acetic acid, as solvent.

The process proceeds in short reaction times without the formation of interfering byproducts to give quantitative or virtually quantitative yields of the appropriate phosphine oxides; however, the elementary sulfur formed during the reaction is not always produced in a form which can be sufficiently well separated by filtration.

In attempting to improve or modify this process so that the elementary sulfur formed during the reaction is produced in a form which can be more easily filtered, it has now been found that this aim can be achieved by use of a solvent which comprises about 2 to 20% by weight of—optionally halogenated—lower aliphatic carboxylic acids and the remainder of mono- or polyhydric aliphatic or cycloaliphatic alcohols—if appropriate in mixtures with other inert solvents which are miscible with the carboxylic acid/alcohol mixture.

The invention therefore relates to a process for the preparation of tertiary phosphine oxides by oxidative treatment of teriatry phosphine sulfides using hydrogen peroxide in a solvent; the process comprises using a solvent which contains about 2 to 20% by weight, preferably about 10 to 20% by weight, of—optionally halogenated—lower aliphatic carboxylic acids and the remainder of mono- or polyhydric aliphatic or cycloaliphatic alcohols—if appropriate in mixtures with other inert solvents which are miscible with the carboxylic acid/alcohol mixture.

The process proceeds—like that according to the previously mentioned patent application—without formation of interfering byproducts to give quantitative or virtually quantitative yields of the appropriate phosphine oxides. Although the reaction times are not always as short as those in the process according to the previously mentioned patent application, they are, however, still shorter than the reaction time in the process of A. M. Aguiar et al., loco cit. The sulfur formed during the reaction is now produced in a finely crystalline form which can be filtered very easily.

With respect to the longer reaction time and the only moderate yield during the oxidation using H₂O₂ in methanol according to A. M. Aguiar et al., loco cit., and with respect to the sulfur of reaction which is not always produced in a form which can be adequately easily filtered according to the process of the previously mentioned patent application, this result was totally unexpected and surprising.

Suitable optionally halogen-substituted lower aliphatic carboxylic acids are preferably aliphatic $C_1$–$C_6$-carboxylic acids, which can be substituted by one or more halogen atoms, preferably F and/or Cl. Examples of such carboxylic acids are:
formic acid
acetic acid
propionic acid
monochloroacetic acid
monofluoroacetic acid
trifluoroacetic acid, etc.

The carboxylic acids can be used both individually and also in mixtures with one another. They should amount to about 2-20% by weight, preferably about 10-20% by weight, of the total solvent. A particularly preferred carboxylic acid is acetic acid (glacial acetic acid).

The remainder of the solvent comprises mono- or polyhydric aliphatic or cycloaliphatic alcohols, optionally in mixtures with other inert solvents which are miscible with the carboxylic acid/alcohol mixture.

Preferred mono- or polyhydric aliphatic or cycloaliphatic alcohols are mono- and dihydric alcohols, having 1 to 8 carbon atoms, which can optionally be further substituted by inert groups. Examples of such alcohols are:
methanol
ethanol
n-propanol
i-propanol
n-butanol
i-butanol
tert.-butanol
2-chloroethanol
ethylene glycol
ethylene glycol monomethyl ether
cyclohexanol, etc.

The alcohols can be used alone or in mixtures with one another. Particularly preferred alcohols are methanol and/or ethanol.

The alcohols can—together with the previously mentioned carboxylic acids—form the entire solvent; however, they can also be used together with other inert solvents. In the latter case, it is preferable for the alcohols to be the major component.

The other inert solvents must be miscible with the carboxylic acid/alcohol mixture; they must, of course, not react in an undesired fashion with the hydrogen peroxide or the starting materials and final products of the reaction. Suitable inert solvents of this type are preferably lower aliphatic, cycloaliphatic and/or aromatic hydrocarbons and/or chlorohydrocarbons (hexane, cyclohexane, toluene, xylene, ethylene chloride, 1,2-dichloroethane, chlorobenzene, fluorobenzene, etc.).

In principle, all possible tertiary phosphine sulfides can be employed as tertiary phosphine sulfides for the process. The use of phosphine sulfides of the formula

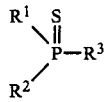

in which $R^1$, $R^2$ and $R^3$ = independently of one another, $C_1$–$C_{12}$-alkyl, $C_6$–$C_{10}$-aryl and $C_6$–$C_{20}$-aralkyl groups which are optionally substituted by inert groups, is preferred.

When the alkyl, aryl and aralkyl groups are substituted by inert groups, the substituents are preferably halogen atoms, particularly only F and/or Cl atoms. Preferred inert substituents for the aryl and aralkyl groups are also alkyl radicals (preferably having up to 4 carbon atoms).

Examples of tertiary phosphine sulfides are:
triphenylphosphine sulfide
diphenyl-methyl-phosphine sulfide
dimethyl-phenyl-phosphine sulfide
tris-(4-fluorophenyl)-phosphine sulfide
bis-(4-fluorophenyl)-(2-fluorophenyl)-phosphine sulfide
bis-(4-fluorophenyl)-phenyl-phosphine sulfide
(4-fluorophenyl)-(2-fluorophenyl)-phenyl-phosphine sulfide
diphenyl-(4-fluorophenyl)-phosphine sulfide
diphenyl-(3-fluorophenyl)-phosphine sulfide
bis-(4-fluorophenyl)-methyl-phosphine sulfide
(4-fluorophenyl)-(2-fluorophenyl)-methyl-phosphine sulfide
dimethyl-(4-fluorophenyl)-phosphine sulfide
bis(4-fluorophenyl)-(4-methylphenyl)-phosphine sulfide
bis-(4-fluorophenyl)-(2-methylphenyl)-phosphine sulfide
(4-fluorophenyl)-(2-fluorophenyl)-(4-methylphenyl)-phosphine sulfide
bis-(4-methylphenyl)-(4-fluorophenyl)-phosphine sulfide
(4-fluorophenyl)-(4-methylphenyl)-(2-methylphenyl)-phosphine sulfide
tris-(4-chlorophenyl)-phosphine sulfide
bis-(4-chlorophenyl)-(2-chlorophenyl)-phosphine sulfide
bis-(4-chlorophenyl)-phenyl-phosphine sulfide
(4-chlorophenyl)-(2-chlorophenyl)-phenyl-phosphine sulfide
diphenyl-(4-chlorophenyl)-phosphine sulfide
bis-(4-chlorophenyl)-methyl-phosphine sulfide
(4-chlorophenyl)-(2-chlorophenyl)-methyl-phosphine sulfide
dimethyl-(4-chlorophenyl)-phosphine sulfide
(4-chlorophenyl)-methyl-phenyl-phosphine sulfide
(4-fluorophenyl)-(4-chlorophenyl)-phenyl-phosphine sulfide
(4-fluorophenyl)-(4-chlorophenyl)-methyl-phosphine sulfide
(4-fluorophenyl)-methyl-phenyl-phosphine sulfide
tris-(4-methylphenyl)-phosphine sulfide
bis-(4-methylphenyl)-(2-methylphenyl)-phosphine sulfide
bis-(4-methylphenyl)-(3-methylphenyl)-phosphine sulfide
bis-(4-methylphenyl)-phenyl-phosphine sulfide
(4-methylphenyl)-(2-methylphenyl)-phenyl-phosphine sulfide
(4-methylphenyl)-(3-methylphenyl)-phenyl-phosphine sulfide diphenyl-(4-methylphenyl)-phosphine sulfide
diphenyl-(3-methylphenyl)-phosphine sulfide
diphenyl-(2-methylphenyl)-phosphine sulfide
bis-(4-methylphenyl)-methyl-phosphine sulfide
(4-methylphenyl)-(2-methylphenyl)-methyl-phosphine sulfide
(4-methylphenyl)-(3-methylphenyl)-methyl-phosphine sulfide
dimethyl-(4-methylphenyl)-phosphine sulfide
dimethyl-(2-methylphenyl)-phosphine sulfide
dimethyl-(3-methylphenyl)-phosphine sulfide.

Hydrogen peroxide can be employed as an approximately 3 to 85% strength aqueous solution, expediently in the commercially available form (about 30 to 35% strength). The hydrogen peroxide is preferably used in approximately equimolar amounts, relative to the starting phosphine sulfide. A slight excess of about 5–40% is advantageous; greater excesses are possible, but, should the occasion arise, are only still of advantage when working with high proportions of alcohols in the solvent mixture.

The phosphine sulfides are dissolved or suspended in the solvent. The ratio of phosphine sulfide:solvent can vary within wide limits. A weight ratio of about 1:(1–20) is advantageous. Hydrogen peroxide, as an aqueous solution, is metered into the solution or suspension at temperatures of in general, between about −5° and +100° C., preferably between about +40° and +80° C. Since the reaction proceeds exothermally, cooling may be necessary. Accordingly, cold solutions or suspensions of phosphine sulfides do not have to be heated to achieve the desired reaction temperature; rather it is possible to use the heat of reaction itself to attain the desired temperature.

The reaction mixture is worked up in a fashion which is known per se by filtration or filtration under suction of the cooled solution to remove the sulfur which is produced here in elementary, finely crystalline form.

The very sparing solubility of elementary sulfur in the solvent mixtures used according to the invention and the good solubility of tertiary phosphine oxides in precisely these mixtures, even in the presence of the water which is unavoidably produced by the reaction procedure, has a particularly favorable effect here. This is particularly true for solvent mixtures of acetic acid and methanol.

After removal of the solvent by distillation (preferably in vacuo), the phosphine oxides usually remain initially as oily carboxylic acid adducts. The free phosphine oxides can easily be obtained in pure form by heating in vacuo or distillation. Likewise, it is possible to stir the carboxylic acid adducts in water and, if appropriate, to cleave them by neutralization using bases. The free phosphine oxides precipitate from the aqueous, optionally alkaline solution and can be filtered off or, if they are liquid, separated off—if appropriate after addition of a solvent which is not water-miscible.

Because the reaction is simple to carry out and because of the relatively short reaction times, the unproblematic work-up, the low pollutant levels (only sulfur and water are produced as byproducts) and the high phosphine oxide yields, the process represents a considerable advance in this area.

The following examples are intended to describe the invention in greater detail.

EXAMPLE 1

717 g of a mixture of 0.10 mol of diphenyl-4-chlorophenyl-phosphine sulfide
0.06 mol of (3-chlorobenzyl)-(4-chlorophenyl)-phenyl-phosphine sulfide
0.10 mol of (2-chlorophenyl)-(4-chlorophenyl)-phenyl-phosphine sulfide
1.50 mol of bis-(4-chlorophenyl)-phenyl-phosphine sulfide
0.09 mol of tris-(4-chlorophenyl)-phenyl-phosphine sulfide, and a total of
0.05 mol of further P=S compounds, which were not identified individually were suspended in 1350 ml (=1.070 g) of methanol/150 ml (=157 g) of glacial acetic acid and a total of 230 g of 35% strength hydrogen peroxide (2.68 mol=41% excess relative to the phosphorus components employed) were added dropwise at 50° C. within 8 hours. When P=S compounds could no longer be detected, any peroxides present were destroyed using 10 g of sodium sulfite, the reaction mixture was cooled and sulfur was filtered off (filtration duration: 6 minutes).

After removal of the solvent by distillation, the residue was washed with sodium hydroxide solution and then twice with water, and the product was distilled at 0.1 mbar to a bottom temperature of 260° C. 630 g of a product with the following composition were obtained:
5.51% of diphenyl-(4-chlorophenyl)-phosphine oxide
3.25% of (3-chlorophenyl)-(4-chlorophenyl)-phenyl-phosphine oxide
5.52% of (2-chlorophenyl)-(4-chlorophenyl)-phenyl-phosphine oxide
78.84% of bis-(4-chlorophenyl)-phenyl-phosphine oxide
4.78% of tris-(4-chlorophenyl)-phosphine oxide.

This corresponds to a yield of 96.2% of theory.

EXAMPLE 2

25 g (0.136 mol) of ethyl-methyl-phenyl-phosphine sulfide were dissolved in
50 g of methanol and
6.3 g of glacial acetic acid, and
11.69 ml (13.21 g=0.136 mol) of 35% strength hydrogen peroxide were added dropwise at 45°–50° C. After cooling, the mixture was filtered and the filtrate was distilled.
20.59 g (0.122 mol) of ethyl-methyl-phenyl-phosphine oxide of boiling point 125° C. at 0.4 mbar and melting point 48° C. were obtained.
Yield: 90% of theory.

I claim:

1. A process for the preparation of tertiary phosphine oxides which comprises treating a tertiary phosphine sulfide using hydrogen peroxide in a solvent which contains about 2 to 20% by weight, of at least one lower aliphatic carboxylic acid, and the remainder of at least one mono- or polyhydric aliphatic or cycloaliphatic alcohol.

2. The process as claimed in claim 1, wherein the tertiary phosphine sulfide is a compound of the formula

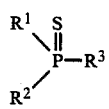

in which $R^1$, $R^2$ and $R^3$ are, independently of one another, $C_1$-$C_{12}$-alkyl, $C_6$-$C_{10}$-aryl or $C_6$-$C_{20}$-aralkyl groups which are unsubstituted or substituted by groups inert in the reaction.

3. The process as claimed in claim 1, wherein the solvent mixture contains at least one further solvent which is inert towards the reactants and and miscible with the carboxylic acid/alcohol mixture.

4. The process as claimed in claim 3, wherein aliphatic, cycloaliphatic, aromatic hydrocarbons, chlorohydrocarbons or mixtures thereof are used as the further solvent.

5. The process as claimed in claim 1, wherein the carboxylic acid has from 1–6 carbon atoms.

6. The process as claimed in claim 1, wherein acetic acid is used as lower aliphatic carboxylic acid.

7. The process as claimed in claim 1, wherein the lower carboxylic acid is a halogenated carboxylic acid.

8. The process as claimed in claim 1, wherein the lower carboxylic acid is a halogenated acetic acid.

9. The process as claimed in claim 1, wherein mono- or dihydric alcohols having 1–8 carbon atoms are used as mono- or polyhydric aliphatic or cycloaliphatic alcohols.

10. The process as claimed in claim 1, wherein methanol, ethanol or a mixture thereof is used as aliphatic alcohol.

11. The process as claimed in claim 1, wherein the lower aliphatic carboxylic acid has from 1 to 6 carbon atoms, is halogenated or not halogenated and is present in an amount of from 10 to 20 percent by weight, referred to the solvent mixture.

12. The process as claimed in claim 1, wherein the hydrogen peroxide is employed in approximately equimolar amounts or in a slight excess, relative to the starting phosphine sulfide.

13. the process as claimed in claim 1, wherein the oxidative treatment is carried out at a temperature between about $-5°$ and $+100°$ C.

14. The process as claimed in claim 1, wherein the oxidative treatment is carried out at a temperature between about $+40°$ and $+80°$ C.

15. A process for the preparation of tertiary phosphine oxides which comprises treating a tertiary phosphine sulfide of the formula

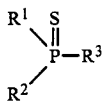

in which $R^1$, $R^2$ and $R^3$ are, independently of one another, $C_1$–$C_{12}$-alkyl, $C_6$–$C_{10}$-aryl or $C_6$–$C_{20}$-aralkyl groups which are unsubstituted or substituted by groups inert in the reaction using hydrogen peroxide in a solvent which contains about 2 to 20% by weight of at least one lower aliphatic carboxylic acid having 1–6 carbon atoms which is not halogenated, and the remainder of at least one mono- or dihydric alcohol having 1–8 carbon atoms, the mixture being free from or containing at least one further solvent which is inert towards the reactants and miscible with the carboxylic acid/alcohol mixture, the oxidative treatment being carried out at a temperature between about $-5°$ and $+100°$ C.

16. The process as claimed in claim 15, wherein acetic acid is used as lower aliphatic carboxylic acid.

17. The process as claimed in claim 15, wherein methanol, ethanol or a mixture thereof is used as aliphatic alcohol.

18. The process as claimed in claim 15, wherein the lower aliphatic carboxylic acid is present in an amount of from 10 to 20% by weight, referred to the solvent mixture.

19. A process for the preparation of tertiary phosphine oxides which comprises treating a tertiary phosphine sulfide of the formula

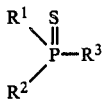

in which $R^1$, $R^2$ and $R^3$ are, independently of one another, $C_1$–$C_{12}$-alkyl, $C_6$–$C_{10}$-aryl or $C_6$–$C_{20}$-aralkyl groups which are unsubstituted or substituted by groups inert in the reaction using hydrogen peroxide in a solvent which contains about 10 to 20% by weight of acetic acid, and the remainder comprises methanol, ethanol or a mixture thereof, the oxidative treatment being carried out at a temperature between about $-5°$ and $+100°$ C.

* * * * *